United States Patent
Courter, Jr.

(10) Patent No.: US 10,175,446 B1
(45) Date of Patent: Jan. 8, 2019

(54) LENS MOUNT APPARATUS AND METHOD

(71) Applicant: Lawrence Leroy Courter, Jr., Costa Mesa, CA (US)

(72) Inventor: Lawrence Leroy Courter, Jr., Costa Mesa, CA (US)

( * ) Notice: Subject to any disclaimer, the term of this patent is extended or adjusted under 35 U.S.C. 154(b) by 44 days.

(21) Appl. No.: 14/872,854

(22) Filed: Oct. 1, 2015

(51) Int. Cl.
| | |
|---|---|
| *G02B 7/02* | (2006.01) |
| *G02B 1/04* | (2006.01) |
| *G02C 9/00* | (2006.01) |
| *B29C 45/00* | (2006.01) |
| *B29L 11/00* | (2006.01) |

(52) U.S. Cl.
CPC .......... *G02B 7/021* (2013.01); *B29C 45/0003* (2013.01); *G02B 1/041* (2013.01); *G02C 9/00* (2013.01); *B29L 2011/0016* (2013.01)

(58) Field of Classification Search
CPC ...................................................... G02B 7/021
USPC ........................................................ 359/726
See application file for complete search history.

(56) References Cited

U.S. PATENT DOCUMENTS

| | | | |
|---|---|---|---|
| 6,502,937 B2 | 1/2003 | Yang | |
| 7,641,333 B2 | 1/2010 | Blanshay et al. | |
| 8,025,395 B2 | 9/2011 | Quintana | |
| 8,814,349 B2 | 8/2014 | Goebel Quintana | |
| 2007/0252942 A1* | 11/2007 | Collier | G02C 9/00 351/41 |
| 2012/0140162 A1* | 6/2012 | Chen | A61F 9/025 351/57 |
| 2015/0131047 A1* | 5/2015 | Saylor | G02B 1/11 351/44 |

* cited by examiner

*Primary Examiner* — James Jones
(74) *Attorney, Agent, or Firm* — Lodestone Legal Group; Jeromye V. Sartain (57) ABSTRACT

A lens mount apparatus comprising a molded first lens component and a second lens component formed integrally with the first lens component through injection-compression molding the second lens component on the first lens component in a secondary operation, resulting in mechano-chemical attachment of the second lens component on the first lens component to produce the unitary lens mount apparatus without compromising the lens mount apparatus optics, wherein at least one of the first and second lens components is an optical lens.

8 Claims, 4 Drawing Sheets

LENS MOUNT APPARATUS AND METHOD

RELATED APPLICATIONS

Not applicable.

BACKGROUND

The subject of this patent application relates generally to structures and manufacturing techniques for lenses and related mounting supports, and more particularly to lens mount apparatuses and methods configured for producing lenses with integral mounting supports yet without compromising the lens optics.

Applicant(s) hereby incorporate herein by reference any and all patents and published patent applications cited or referred to in this application.

By way of background, lenses are generally classified by the curvature of the two (front and back) optical surfaces, each of which are typically spherical, or made up of a part of the surface of a sphere. A lens is biconvex if both surfaces are convex, biconcave if both surfaces are concave, or concave-convex or meniscus if one surface is convex and the other surface is concave. If one of the surfaces is flat, the lens is plano-convex or plano-concave depending on the curvature of the surface of the lens opposite the flat surface. The most common type of lens in ophthalmology or for use as a "corrective" or "prescription" lens is essentially a positive meniscus. Other kinds of specialized lenses include toric or sphero-cylindrical lenses and aspheric lenses, having one or more non-spherical surfaces, cylindrical lenses, Fresnal lenses, lenticular lenses, gradient index lenses, axicons, and superlenses.

The process of forming finished lenses of virtually any shape or configuration has traditionally been accomplished through a glass lens blank manufacturing process or essentially a casting process wherein a glass powder is melted and poured into the lens blank cavity and then annealed. More recently, with the advent and improved technology of thermoplastic materials such as polycarbonate, injection molding of lens blanks has become the preferred method of producing many kinds of lenses, including ophthalmic or corrective or prescription lenses. In either case—glass or plastic—where corrective lenses are to be formed, the "prescription" curvature is cut or ground into the lens blank to produce the finished lens with the desired optical properties. The challenge in both initially forming the lens blank and then in cutting into the blank the desired curvature to form the finished lens is to not introduce distortion or stress into the lens that would adversely affect its optical qualities.

As is known, finished lenses in the case of traditional ophthalmic use are then mounted in frames or support structure of some kind so as to be worn for effective optical performance, such as vision correction in the case of traditional eyewear with nose and ear pieces. In this application, the lenses are effectively snapped into position within eyewear frames, such as within inwardly-opening retention grooves of the frame designed to match the perimeter or profile of the lens, or the lens cut to match the frame profile, or the lenses are otherwise mounted or secured by screwing or fastening a retaining member to the main part of the frame so as to clamp the lens in place. Even lenses in other contexts such as telescopes or microscopes must be mounted or held in the desired position for the passage of light therethrough or the reflection of light thereof. Oftentimes, corrective lenses are incorporated into or used in conjunction with further lenses, whether for additional optical properties or to provide a protection or safety function or both, such as in protective helmets, hoods, face shields, visors and the like or simply as part of eyewear for sports or other recreational use such as sunglasses and goggles. Other contexts for lenses in this modern age relate to "virtual reality" headsets, "heads up" displays, and the like. In virtually all such contexts, it is desirable to not just produce but be able mount the lens within a support structure whereby the lens may be held and positioned where needed without causing any distortion or otherwise adversely affecting the optical properties of the lens.

In short, the variety and increasing complexity of lens applications and the attendant challenges of properly manufacturing and mounting such lenses has resulted in needs that have heretofore gone unmet in the industry.

As further background, U.S. Pat. No. 8,814,349 entitled "One-Piece Lens with Surplus Inner Optical Material" is directed to a one-piece lens made from optical material that includes an outside part and an inside part, in which the inside parts comprise a surplus amount of the same optical material as the lens, for the purpose of cutting ophthalmic lenses, the surplus material being positioned close to the central part of the lens. While there is thus provided at least some teaching of a unitary lens construction having an inner prescription lens portion and a relatively larger outer lens portion, no provision is made for integrating or forming the lens with any mounting supports, much less doing so without compromising the lens optics.

U.S. Pat. No. 8,025,395 entitled "Industrial Safety Goggles with Frame for Ophthalmic Micas and Impact Protection Mica" is directed to industrial safety goggles provided with permanent ophthalmic micas having a full impact protection mica positioned thereon, wherein the impact protection mica is made from polycarbonate, providing protection against ultraviolet rays and can be removed, thereby enabling the frames to be used as ophthalmic glasses. The goggles include a ventilation area and the ophthalmic micas have an improved visual field owing to the design of the frame to which they are mounted and fixed using angular incisions in the frame. The frame is provided with an open space at both eyes between the mica and the end of the rim, which provides ventilation and prevents the fogging of the graduated micas.

U.S. Pat. No. 7,641,333 entitled "Protective Eyewear Including Auxiliary Lenses" is directed to an eyewear assembly including an outer first frame, at least one outer first lens, an inner second frame, and at least one inner second lens. The assembly includes a mechanism for holding the first frame and first lens in front of a user's face. The second frame has a mechanism for attachment to the first frame, to hold the second frame between the user's eyes and the first lens. The at least one second lens is carried by the second frame. The second frame includes a first frame portion that mounts the second lens and a second frame portion over-molded onto the first frame portion defining portions of the outside surface area of the second frame. The first frame portion is of a relatively hard material and the second frame portion is of a relatively soft material. A shock-absorbing pad can be fit between the first and second frames.

U.S. Pat. No. 6,502,937 entitled "Eyewear with Prescription Lens Inserts" is directed to eyewear comprising an eyewear frame, at least one lens in the eyewear frame, and an attachment device for holding a prescription lens insert so that the prescription lens insert is held in position adjacent the lens of the eyewear thereby to correct the vision of a wearer of the eyewear.

Once more, the art neither discloses nor suggests lens mount apparatuses and methods configured for producing lenses with integral mounting supports yet without compromising the lens optics as by inducing stresses or distortion in the lens. Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing a lens mount apparatus. In at least one embodiment, the lens mount apparatus comprises a molded first lens component and a second lens component formed integrally with the first lens component through injection-compression molding the second lens component on the first lens component in a secondary operation, resulting in mechanochemical attachment of the second lens component on the first lens component to produce the unitary lens mount apparatus without compromising the lens mount apparatus optics, wherein at least one of the first and second lens components is an optical lens.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

As a threshold matter, it is noted that when the word "lens" or the phrase "optical lens" is used herein, any optical member, or component having defined optical qualities, is intended to be included, whether such lens is transparent or clear, translucent or tinted, opaque, or reflective or mirrored, or any combination thereof, and whether with respect to light passing in one direction, both directions, or any direction through the lens or reflecting off of the lens, so long as the lens has certain designed and intended optical properties for transmitting or reflecting light in a desired fashion to suit a particular optics application, such that distortion in the lens is to be avoided as potentially or actually adversely affecting the optical performance of the lens. Any such lens as contemplated herein may be made of any material and be of any geometry or thickness to suit any application, whether now known or later developed. Accordingly, "lens" as used throughout is to be understood as having a broader meaning than its typical or standard definition and to include or encompass, again, any component having defined or intended optical qualities or functioning as an optical device.

Figure 1:
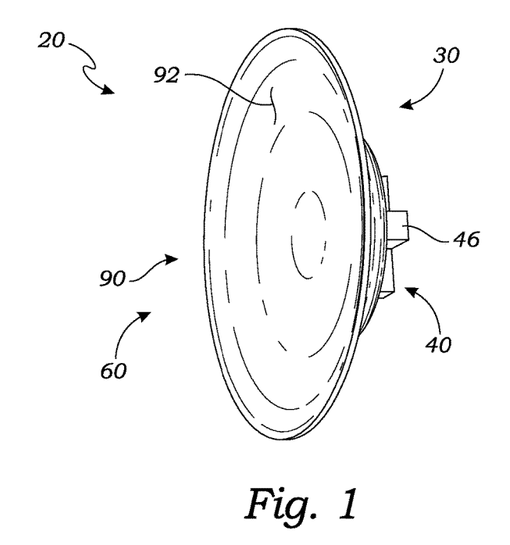
FIG. 1 is a perspective view of an exemplary lens mount apparatus, in accordance with at least one embodiment.

Referring now to FIG. 1, there is shown a perspective view of an exemplary embodiment of a lens mount apparatus 20. The apparatus 20 comprises, in the exemplary embodiment, a first lens component 30 and a second lens component 60 formed integrally with the first lens component 30. As shown, the second lens component 60 defines a second perimeter that is greater than the first perimeter defined by the first lens component 30, though it will be appreciated that this is not necessarily the case—that in alternative embodiments the first and second perimeters may be substantially equal or the first perimeter may be greater than the second perimeter. At a high level, it is noted that in the illustrated embodiment of the lens mount apparatus 20 the first lens component 30 is configured as a lens support device 40 having one or more mechanical attachment features 46 for subsequently mounting the integrated second lens component 60 that is here configured as a meniscus optical lens 90 having a concave outer surface 92 and a convex inner surface 94 (FIG. 3) to which the lens support device 40 is attached. It will be appreciated that in such a configuration with the lens support device 40 mounted substantially centrally on the back of the lens 90 that the lens is here configured as having a mirrored or reflective outer surface 92, though not necessarily. It will also be appreciated that throughout the present specification the terms "outer," "front" or "forward" are used interchangeably to describe features or surfaces that are facing or exposed to one direction, such as toward a light source (not shown), and the terms "inner," "back," "inward," or "rear" or "rearward" are used interchangeably to describe features or surfaces that are facing or exposed to a substantially opposite direction, as with the two opposed sides or surfaces of the lens 90. While in theory the first and second lens components 30, 60 may be formed integrally as shown in FIG. 1 as by being molded or otherwise formed in a single "shot," this is not desirable when, as here, one or more of the lens components is to be an optical lens, wherein avoiding sinks, stresses, defects, or other issues within the material that cause distortion and thus would adversely affect the designed or intended optical properties of the particular lens component that are desired. Similarly, simply molding or forming the first and second lens components 30, 60 separately and then bonding, ultrasonically welding, or otherwise fastening them together may also result in an integral assembly as shown, but is again not desirable because of the adverse effects that this would likely have on the optical properties of the finished lens mount apparatus 20, not to mention the added cost and/or labor associated with such a separate assembly step. Advantageously, according to aspects of the present invention, both the first and second lens components 30, 60 are molded in succession, with the second lens component 60 specifically formed integrally with the first lens component 30 through injection-compression molding the second lens component 60 on the first lens component 30 in a secondary operation, resulting in mechanochemical attachment of the second lens component 60 on the first lens component 30 to produce the unitary lens mount apparatus 20 without compromising the lens mount apparatus optics. The result is uniform wall thickness components, and particularly the second lens mount component 60 formed as the optical lens 90, having no distortion and thus preserving the intended optical qualities of the lens.

Figure 2A:
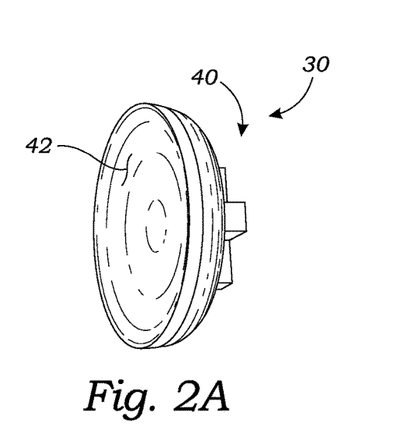
FIG. 2A is a perspective view of a first lens component thereof, in accordance with at least one embodiment.
Figure 2B:
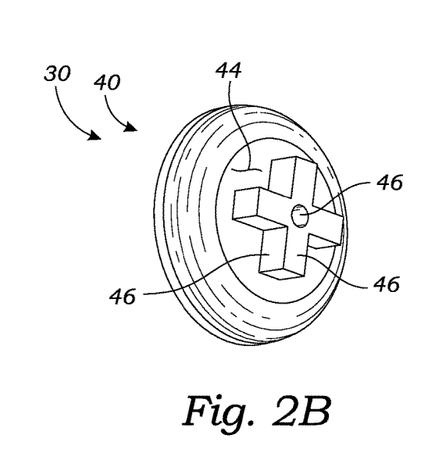
FIG. 2B is a rear perspective view thereof, in accordance with at least one embodiment.
Figure 3:
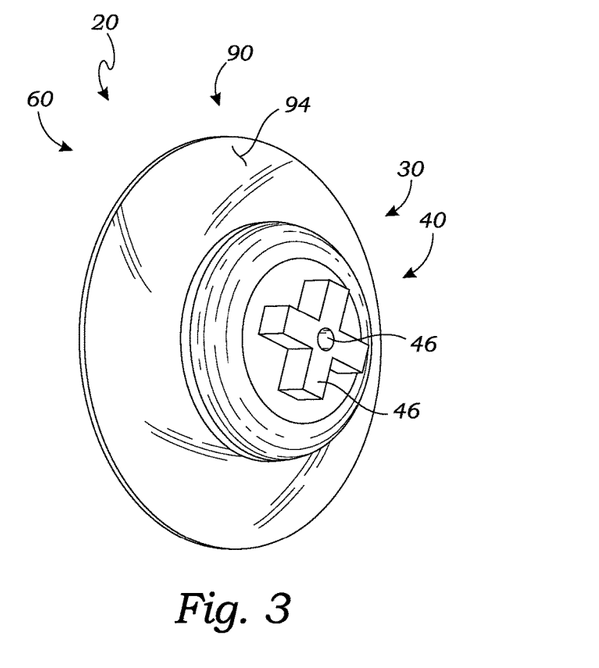
FIG. 3 is a rear perspective view of the lens mount apparatus of FIG. 1, in accordance with at least one embodiment.

Turning now to FIGS. 2A and 2B, there are shown front and rear perspective views of the first lens component 30, again here configured as a lens support device 40. As best seen in FIG. 2A, the lens support device 40 is formed having an outer surface 42 that is substantially concave and thus configured to seat flush with the convex rear or inner surface 94 of the lens 90, best seen in FIG. 3. As illustrated and best seen in FIG. 2B, the rear or inner surface 44 of the lens support device 40 is formed having one or more mechanical attachment features 46 formed thereon or therein. Specifically, shown are both a central hole, which it will be appreciated with reference to FIG. 2A does not pass through the lens support device 40 to the front or outer surface 42 but may be configured with a straight bore of a desired depth to accept a dowel or the like (not shown) as through a press-fit, bonding, or any other such attachment means now known or later developed or may have a threaded bore so as to receive a screw, bolt, or other such threaded fastener now known or later developed. Furthermore, as illustrated, the exemplary mechanical attachment features 46 further comprise a raised, indexing surface that may be keyed to further support structure so as to positively align or prevent the rotation of the lens mount apparatus 20, and the optical lens 90 portion particularly, once in a desired position. It will be appreciated by those skilled in the art that the lens support device 40 and its related mechanical attachment features 46 may take on virtually any form as appropriate for a particular context, such that the exemplary embodiment of FIGS. 1-3 is to be understood as merely illustrative and non-limiting. With continued reference to FIGS. 2A and 2B, the first lens component 30 here configured as the lens support device 40 may be formed through any manufacturing method and employing any appropriate material now known or later developed. Those skilled in the art will appreciate that such a component, if to be plastic, may be formed through an injection or compression-injection molding process as now known or later developed—that all features as shown and described can easily and conventionally be formed through a molding process in a single "shot." According to aspects of the present invention, the first lens component 30 or lens support device 40 may be formed of polycarbonate, though it will be appreciated that any thermoplastic material now known or later developed may be employed.

Referring next to FIG. 3, once the first lens component 30 or lens support device 40 as shown in FIGS. 2A and 2B is formed as by molding, in a secondary operation the second lens component 60 here configured as an optical lens 90 is compression-injection molded directly onto the first lens component 30 to form the lens mount apparatus 20. In a bit more detail, the first lens component 30 may remain in the very same mold cavity and by operation of a slide or otherwise the cavity modified to accommodate a second injection and immediate compression to form and substantially simultaneously effectively fuse the second lens component 60 onto the first lens component 30. Alternatively, the molded first lens component 30 may be placed into an appropriate cavity in a different mold in order to then injection-compression mold the second lens component 60 thereto. In either case, the molded first component 30 may still be warm or may be allowed to cool prior to the second operation of molding the second lens component 60 onto the first lens component 30. It will be appreciated that in either scenario the one or more mechanical attachment features 46 may also serve to index and hold in place the lens support device 40, or first lens component 30, as the second lens component 60 is compression-injection molded thereon. Once more, in the exemplary embodiment, this union to form the integral lens mount apparatus 20 happens between the convex inner surface 94 of the second lens component 60 and the concave outer surface 42 of the first lens component 30. Those skilled in the art will appreciate that the resulting mechanochemical attachment between the first and second lens components 30, 60 is a product of the coupling of mechanical and chemical phenomena on a molecular scale and includes complex transformations induced by pressure and heat, though distinct from usual thermal or photochemical mechanisms. The result is a synthesized or one-piece substantially stress- and distortion-free lens mount apparatus 20 comprising an optically correct polycarbonate lens or mirror surface with no defects or sink marks while having a unitary mounting or fastening structure on the back or other surface of the lens. Again, while the illustrated embodiment entails a symmetrical or round meniscus lens with a substantially centered rear mounting feature that is itself symmetrical, those skilled in the art will appreciate that a virtually infinite variety of lens mount apparatuses according to aspects of the present invention are possible without departing from its spirit and scope.

Turning now to FIGS. 4-8 there is illustrated a further exemplary lens mount apparatus according to aspects of the present invention, here in the context of eyewear and essentially an ophthalmological application. Particularly, as shown in the side perspective view of FIG. 4, the alternative lens mount apparatus 20 is advantageously incorporated into a pair of goggles G, which is particularly beneficial where corrective or prescription lenses are to be installed or formed within the lens mount apparatus 20 as shown and described in connection with the exemplary embodiment of FIGS. 5 and 6. Generally speaking, the finished goggle G includes its own frame F, with the lens mount apparatus 20 here including effectively a third lens component 100 configured as the outermost front lens 110 of the goggle G, more about which is said below, particularly in connection with the exploded perspective view of FIG. 8.

Figure 5:
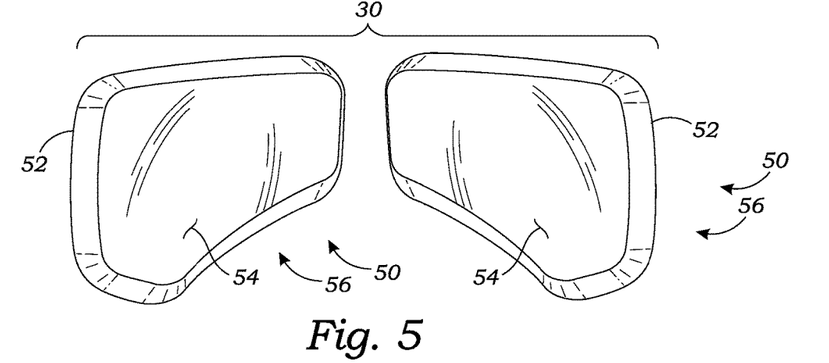
FIG. 5 is a rear perspective view of a first lens component thereof, in accordance with at least one embodiment.

Referring to FIG. 5, there is shown a rear perspective view of the first lens component 30 here as first optical lenses 50 configured as a pair of lens inserts 56. The lens inserts 56 are shown as being essentially mirror images of one another, as essentially left and right lenses 50. The lens inserts 56 may again be formed from any appropriate manufacturing method and material now known or later developed. In the exemplary embodiment the inserts 56 are injection or compression-injection molded from clear polycarbonate. These lens inserts 56 may be formed of virtually any size and shape to suit any particular finished eyewear context, here they being sized and shaped to be narrower toward the middle or the bridge of the nose area when worn and wider toward the temples again when worn so as to have a somewhat trapezoidal shape. The thickness of the lens inserts 56 is a function of both the finished eyewear geometry and the specifications for cutting or grinding the appropriate curvature into the lenses to satisfy what has been prescribed for correction of the wearer's vision. Each lens insert 56 generally has a meniscus curvature, again meaning that the lens outer surface 52 is convex and the lens inner surface 54 is concave, which is typical for corrective or prescription lenses in finished form. As shown, the perimeter of each lens insert may be beveled to assist removal from the mold. It will be appreciated that at this stage the polycarbonate lens inserts 56 form or define lens blanks that may be subsequently machined or cut to a particular curvature in the nature of prescription or corrective lenses. Accordingly, the optical quality of the lens inserts 56 in terms of being free of voids, sinks, stresses, or any other defects must be maintained to render the inserts 56 useful in fashioning prescription lenses. Were the lenses 50 to be mounted in conventional eyewear frames they may then be simply sent to the optometrist or the like for grinding to suit a particular patient and then installed in the selected eyewear frames. However, even in that scenario, the installation of the lenses after they have been ground can induce stresses that adversely affect the lens optics. As such, it would still be preferable to have the frame or mounting features formed integrally with the lenses 50 and in so doing not induce any stresses or distortion in accordance with aspects of the present invention so that after the prescription curvature is ground into the lenses 50, since they already have the necessary frame or at least mounting features formed integrally with the lenses, completion of the eyewear is as simple as attaching other frame features such as the temple pieces. In the exemplary goggle context, the idea is much the same—to incorporate a second lens component 60 formed as a second lens support device 70 integrally on the first lens component 30 here formed as optical lenses 50 so as to form a lens sub-assembly that can then be installed within the goggle G.

Figure 4:
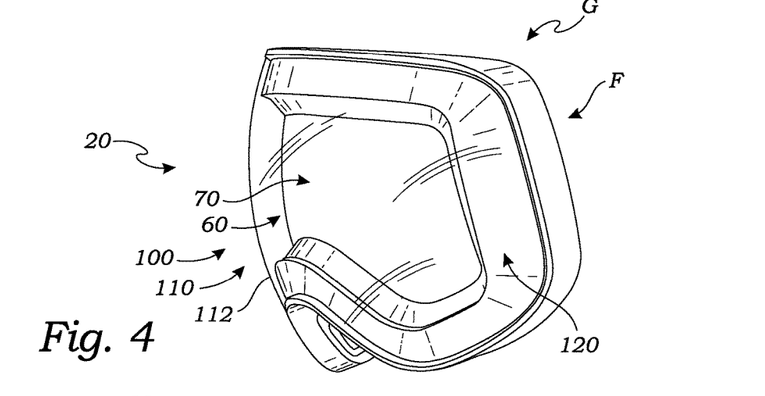
FIG. 4 is a side perspective view of an alternative exemplary lens mount apparatus incorporated within a goggle, in accordance with at least one embodiment.
Figure 6:
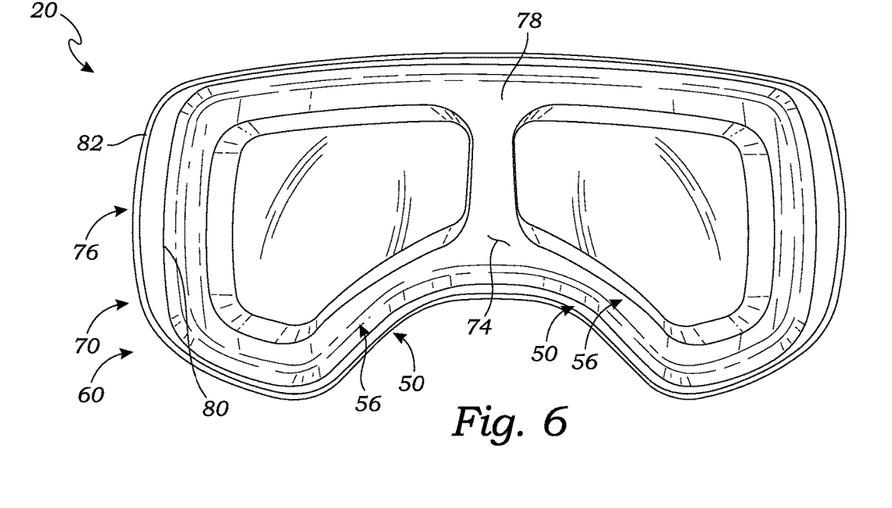
FIG. 6 is a rear perspective view of the lens mount apparatus thereof, in accordance with at least one embodiment.

Turning to FIG. 6, then, there is now shown a rear perspective view of the lens mount apparatus 20 wherein the second lens component 60 in the form of a lens support device 70 is formed integrally on the first lens component 30 in the form of the first optical lenses 50 defining a pair of lens inserts 56 as by compression-injection molding the second lens component 60 on the first lens component 30 (i.e., forming the lens support device 70 on or over the lens inserts 56). As noted in connection with the embodiment of FIGS. 1-3, the compression-injection molding of the second lens component 60 may be in the same mold in which the lens inserts 56 are molded or may be in a separate mold having a cavity to accommodate the inserts 56 in the desired relative positions, and may be with the inserts 56 still warm or cooled first. In either case, the second lens component 60 in the form of the lens support device 70 is formed so as to essentially fuse the pair of lens inserts 56 to the rear or inner surface 74 thereof as shown. Particularly, it will be appreciated that the somewhat concave curvature of the inner surface 74 of the lens support device 70 substantially conforms to the somewhat convex lens outer surface 52. In the exemplary embodiment, the lens support device 70 is also formed of clear polycarbonate, resulting in a one-piece, monolithic or homogeneous lens sub-assembly having the desired optical quality of no induced stresses, sinks, or other defects, such that as noted above, when a prescription curvature is subsequently ground into the rear or inner surfaces 54 of the lenses 50, or lens blanks 56, no defects or sinks or other issues are encountered and the desired optical properties are achieved, with the resulting prescription sub-assembly then ready for installation into a finished eyewear such as the goggle G (FIG. 4). Notably, the lens support device 70 also then functions as a second optical lens, with the resulting lens sub-assembly essentially comprising a "shield" or "near net-shape" lens for which no perimeter cutting or shaping would be necessary, as distinct from lens blanks that are to be machined to the desired final shape, thereby reducing the amount of material used and scrapped. It will be appreciated that such a lens sub-assembly or lens mount apparatus 20 may be configured so as to then be attached in final form to an eyewear frame with appropriate attachment means, versus the attachment means shown and described herein as incorporated into the lens support device 70 for the purpose of later assembling the lens mount apparatus 20 within a pair of goggles G (FIG. 4). Accordingly, in the exemplary embodiment, the lens support device 70 is defined by a front or outer lens wall 78 that covers the inner prescription lenses 50. The lens wall 78 further defines a lens wall perimeter 80 having a perimeter flange 82 that extends substantially inwardly. In the exemplary embodiment, in forming the lens support device 70, the at least one mechanical attachment feature 76 is configured in the form of the lens perimeter flange 82. It will be appreciated that the perimeter flange 82 may itself be formed with further attachment features such as notches or holes as required or desired. The shape and depth of the perimeter flange 82 may also vary depending on a number of factors related to the final eyewear configuration as well as the material and manufacturing method selected. Again, a variety of other such attachment features 76 and the configuration of the perimeter flange 82 itself, if included at all, may be incorporated in a lens mount apparatus 20 according to aspects of the present invention without departing from its spirit and scope, such as to suit other eyewear applications.

Figure 7:
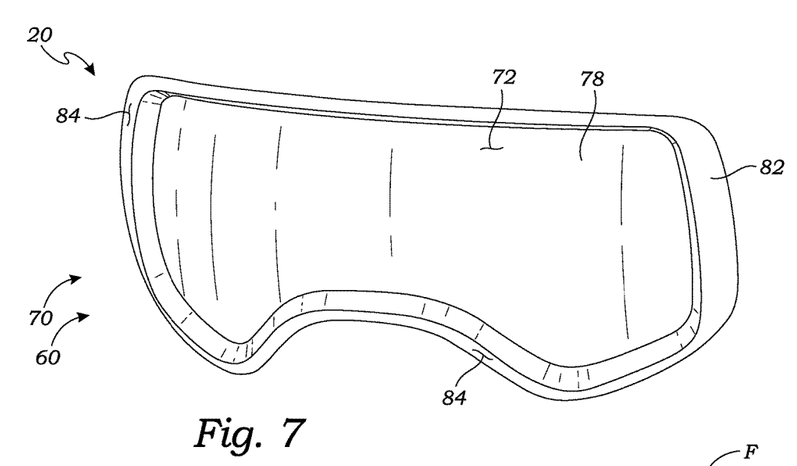
FIG. 7 is a front perspective view thereof, in accordance with at least one embodiment.

Turning briefly to FIG. 7, there is shown a front perspective view of the exemplary lens mount apparatus 20 of FIGS. 4-6. The second lens component 60 is again configured as a lens support device 70 comprising a lens wall 78 that defines the outer surface 72 of the support device 70. Further, about the perimeter of the lens wall 78 there is formed a perimeter flange 82 that as now seen from the front not only extends inwardly or rearwardly but also outwardly or forwardly of the lens wall 78 so as to form or define an outwardly-facing perimeter flange surface 84 offset outwardly of the support device outer surface 72, more about which is said below in connection with FIG. 8. Those skilled in the art will again appreciate that the overall shape of the lens support device 70 and thus the perimeter flange 82 is merely illustrative and that a variety of other configurations are possible without departing from the spirit and scope of the invention.

Figure 8:
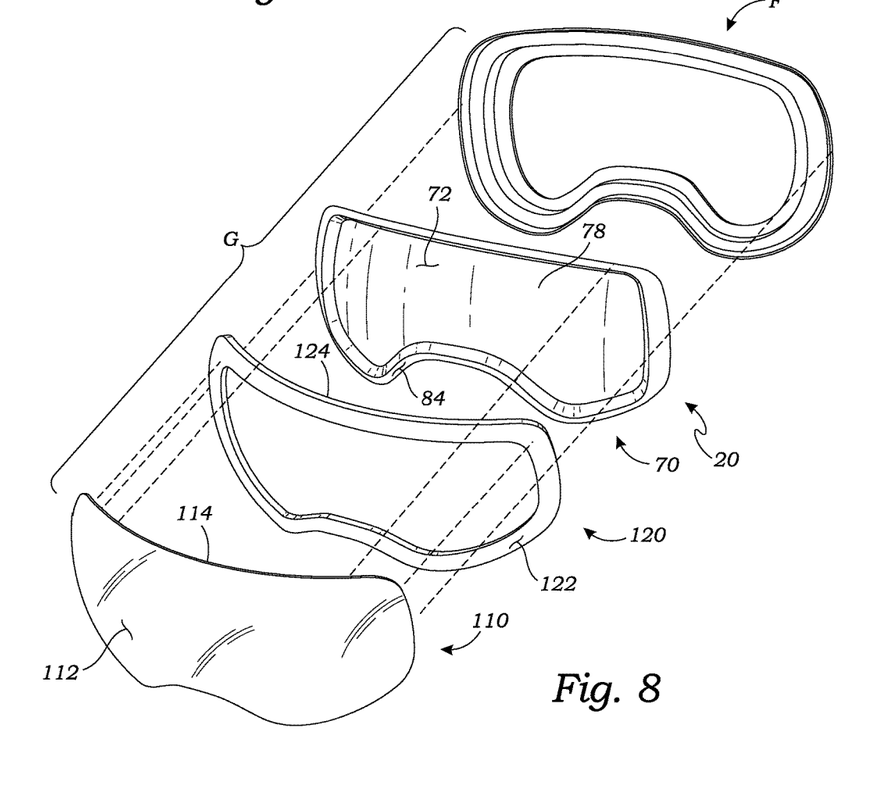
FIG. 8 is an exploded front perspective view thereof, in accordance with at least one embodiment.

With reference now to FIG. 8, there is shown a reduced scale exploded perspective view illustrating the assembly of the lens mount apparatus 20 within a goggle G (FIG. 4). As illustrated, the profiles of the respective components making up the goggle G assembly are substantially the same so that a proper nesting of the components in the finished device is achieved, as shown in FIG. 4. It is particularly noted that in the exemplary embodiment there is included a gasket 120 positioned between the lens mount apparatus 20 and the outer third optical lens 110. More particularly, the perimeter of the gasket 120 is configured to substantially conform to that of both the lens mount apparatus 20 and the outer third optical lens 110, with the inner surface 124 of the gasket configured to substantially seat on and conform to the outwardly-facing perimeter flange surface 84 of the lens mount device 70 and the outer surface 122 of the gasket 120 configured to substantially seat on the third lens inner surface 114 substantially about its perimeter, thereby effectively securing the third lens 110 on the lens mount apparatus 20. As such, the gasket 120 may be formed of a double-sided adhesive foam or the like for forming such assembly, though of course any other material and method of its attachment now known or later developed is possible. In an alternative embodiment there may be no gasket 120 at all, with instead the outer third lens 110 directly seated or installed on the lens mount apparatus 20. In either case, it will be appreciated that due to the stand-off of the perimeter flange 82 (FIG. 7) from the lens wall 78, there is effectively formed a space or air gap between the support device or lens wall outer surface 72 and the inner surface 114 of the outer third lens 110, which air gap aids in the anti-fogging properties of the lens assembly. Moreover, where the gasket 120 is employed, it will be appreciated that a relatively larger stand-off or space between the support device or lens wall outer surface 72 and the inner surface 114 of the outer third lens 110 is achieved, creating an even larger air gap for anti-fogging functionality. Relatedly, by forming the gasket 120 of an open cell foam that allows for a degree of air exchange between the atmosphere and the bound air gap region of the goggle G between the lens mount apparatus 20 and the front or outer lens 110 further anti-fogging performance is achieved along with an insulation effect. That is, an air exchange or pressure regulation functionality is provided without compromising the anti-fogging and insulation properties of the goggles G. While a particular form or geometrical configuration of the goggle G and particularly the gasket 120 are shown, those skilled in the art will appreciate that the assembly may take a number of other forms without departing from the spirit and scope of the invention. Relatedly, it is possible that the grinding of the prescription curvature on the lens inserts 56 (FIGS. 5 and 6) may take place before or after the front lens 120 is assembled on the lens mount apparatus 20 or even after such sub-assembly is installed within the goggle frame F to complete the assembly of the goggles G. The lens mount apparatus 20 may be installed within the frame F employing any attachment technique or feature now known or later developed, and whether permanent or temporary.

Figure 9:
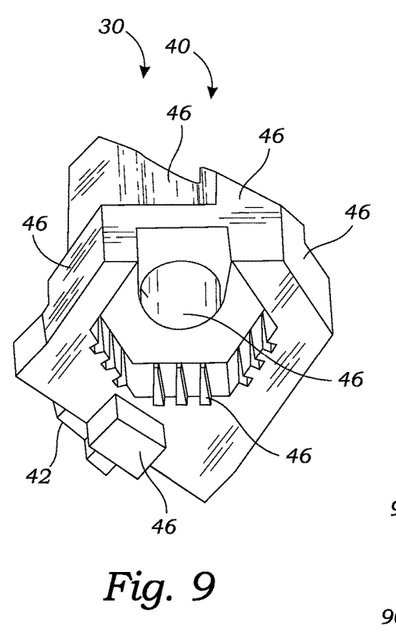
FIG. 9 is a perspective view of a further exemplary first lens component, in accordance with at least one embodiment.
Figure 10:
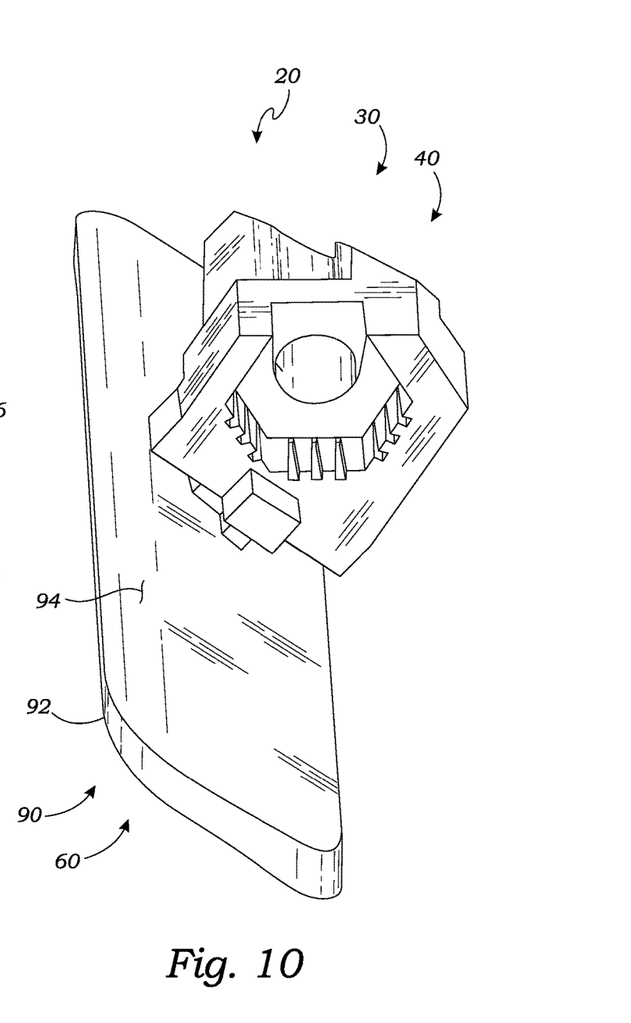
FIG. 10 is a perspective view of an alternative lens mount apparatus incorporating the first lens component of FIG. 9, in accordance with at least one embodiment.

Finally, turning to FIGS. 9 and 10, there are shown perspective views of yet another alternative lens mount apparatus 20 and first and second lens components 30, 60 thereof according to aspects of the present invention. Once more, in this further exemplary embodiment, the first lens component 30 configured as a lens support device 40 is formed first as through an injection molding process. Here, the lens support device 40 is formed having a number of mechanical attachment features 46, including a cross-hole, walls and sloped surfaces, a bracket, a notch, keyed surfaces, and a toothed surface here positioned somewhat circumferentially about the cross-hole. It will be appreciated that all such features 46, alone or in various combinations, may cooperate to later mount the lens support device 40 to other structure as part of a larger assembly and that certain features serve more of a fastening purpose and certain other features more of a location or positioning purpose—any such mechanical fastening features now known or later developed may be incorporated in any such lens support device 40. Here, it will be appreciated that all such features may be formed via injection molding but that even so by having certain regions of greater thickness and a number of "corners" and therefore potential stress points in the material, there is the possibility that stresses, distortions, or other defects might be induced within the part, such that it is again desirable to not also mold any optical lens feature in one "shot" with the lens support device 40 whereby such defects may be found in the optical lens as well. Accordingly, with reference to FIG. 10, there is shown a completed lens mount apparatus 20 wherein the second lens component 60 here configured as a substantially rectangular optical lens 90 is attached or formed integrally with the first lens component 30 configured as the lens support device 40 as through a subsequent compression-injection molding process. In essence, the lens support device 40, once formed, may either remain in the same mold cavity or be transferred to a different mold or cavity and either way be held in a fixed position as the optical lens 90 is molded such that the rear or inner surface 94 of the lens 90 is affixed or fused to the front or outer surface 42 (FIG. 9) of the lens support device 40 in the arrangement of the lens mount apparatus 20 shown in FIG. 10. While the lens 90 is shown as having a particular rectangular profile and thickness and with the lens support device 40 substantially centered thereon, it will again be appreciated that a virtually infinite variety of configurations of the lens 90 and lens support device 40 and their engagement are possible without departing from the spirit and scope of the present invention.

Aspects of the present specification may also be described as follows:

1. A lens mount apparatus comprising a molded first lens component and a second lens component formed integrally with the first lens component through injection-compression molding the second lens component on the first lens component in a secondary operation, resulting in mechano-chemical attachment of the second lens component on the first lens component to produce the unitary lens mount apparatus without compromising the lens mount apparatus optics, wherein at least one of the first and second lens components is an optical lens.

2. The apparatus of embodiment 1 wherein: the first lens component is a lens support device; and the second lens component is an optical lens.

3. The apparatus of embodiment 2 wherein the lens support device is formed as a structural member having at least one mechanical attachment feature.

4. The apparatus of embodiment 3 wherein the at least one mechanical attachment feature is selected from the group consisting of a hole, a wall, a bracket, a key, a keyway, a notch, a sloped surface, and a toothed surface.

5. The apparatus of embodiment 1 wherein: the first lens component is a first optical lens; and the second lens component is a lens support device.

6. The apparatus of embodiment 5 wherein the second lens component is simultaneously a second optical lens, the first and second optical lenses together defining the lens mount apparatus optics.

7. The apparatus of embodiment 6 wherein the first lens component comprises two spaced-apart lens inserts.

8. The apparatus of embodiment 7 wherein each lens insert is configured for being formed as a finished prescription lens in a secondary operation.

9. The apparatus of any of embodiments 2-8 wherein the lens support device comprises: a continuous lens wall defining a lens wall perimeter; and a perimeter flange extending substantially inwardly from at least a portion of the lens wall perimeter, the perimeter flange comprising at least one mechanical attachment feature.

10. The apparatus of embodiment 9, wherein the at least one mechanical attachment feature is selected from the group consisting of a hole, a wall, a bracket, a key, a keyway, a notch, a sloped surface, and a toothed surface.

11. The apparatus of embodiment 9, wherein: the perimeter flange further extends substantially outwardly from at least a portion of the lens wall perimeter so as to define an outwardly-facing perimeter flange surface offset from the lens wall; and a third lens component defining an outer third optical lens is positioned adjacent to the perimeter flange surface so as to form an air gap between the third optical lens and the lens wall of the lens support device.

12. The apparatus of embodiment 11, further comprising an adhesive open-cell foam gasket positioned between the perimeter flange surface and the outer optical lens and thereby attaching the outer optical lens to the lens support device and forming a relatively larger air gap therebetween.

13. The apparatus of any of embodiments 1-12 wherein: the first lens component defines a first perimeter; and the second lens component defines a second perimeter, the second perimeter being greater than or equal to the first perimeter.

14. The apparatus of any of embodiments 1-13 wherein: the first lens component is formed from a first material; and the second lens component is formed from a second material, the first and second materials being the same.

15. The apparatus of embodiment 1 wherein the optical lens has a reflective optical surface so as to form a mirror.

16. A lens mount apparatus comprising: a molded first lens component comprising two spaced-apart lens inserts together forming a first optical lens; and a second lens component comprising a second optical lens defining a continuous outer lens wall having an inner surface and further comprising a lens support device, the second lens component formed integrally with the first lens component through injection-compression molding the second lens component on the first lens component in a secondary operation, resulting in mechanochemical attachment of the second lens component on the first lens component to produce the unitary lens mount apparatus without compromising the lens mount apparatus optics, wherein the lens inserts are fused to the inner surface of the lens wall the resulting first and second optical lenses together define the lens mount apparatus optics.

17. A method of forming a lens mount apparatus comprising the steps of: molding a first lens component; and injection-compression molding a second lens component on the first lens component in a secondary operation, resulting in mechanochemical attachment of the second lens component on the first lens component to produce the unitary lens mount apparatus without compromising the lens mount apparatus optics, wherein at least one of the first and second lens components is an optical lens.

18. The method of embodiment 17 wherein the step of molding the first lens component comprises forming a lens support device having at least one mechanical attachment feature.

19. The method of embodiment 17 wherein the step of molding the first lens component comprises forming two spaced-apart lens inserts, the first lens component being an optical lens.

20. The method of any of embodiments 17-19 wherein the step of injection-compression molding the second lens component on the first lens component comprises forming a lens wall, the second lens component being an optical lens.

In closing, it is to be understood that although aspects of the present specification are highlighted by referring to specific embodiments, one skilled in the art will readily appreciate that these disclosed embodiments are only illustrative of the principles of the subject matter disclosed herein. Because the principles of the specification may be practiced in a number of configurations beyond those shown and described, it is to be understood that the specification is not in any way limited by the exemplary embodiments, but is generally directed to a lens mount apparatus and is able to take numerous forms to do so without departing from the spirit of the specification. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present specification, which is defined solely by the claims. It will also be appreciated by those skilled in the art that the present specification is not limited to the particular geometries and materials of construction disclosed, but may instead entail other functionally comparable structures or materials, now known or later developed, without departing from the spirit of the specification. Accordingly, the present specification is not limited to that precisely as shown and described.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method of forming a lens mount apparatus comprising the steps of:
   molding a first lens component; and
   injection-compression molding a second lens component on the first lens component in a secondary operation, resulting in mechanochemical attachment of the second lens component on the first lens component to produce the unitary lens mount apparatus without compromising the lens mount apparatus optics; wherein:
   one or more of the first and second lens components is formed as an optical lens; and
   one or more of the first and second lens components is formed as a lens support device being a structural member having at least one mechanical attachment feature selected from the group consisting of a hole, a bracket, a key, a keyway, a notch, a toothed surface, and a wall or a sloped surface at an angle to the optical lens.

2. The method of claim 1 wherein the step of molding the first lens component comprises forming two spaced-apart lens inserts, the first lens component being the optical lens.

3. The method of claim 1 wherein the step of injection-compression molding the second lens component on the first lens component comprises forming a lens wall, the second lens component being the optical lens.

4. A lens mount apparatus comprising:
   a first lens component formed as a first optical lens;
   a second lens component formed as a lens support device integrally with the first lens component to produce the unitary lens mount apparatus without compromising the lens mount apparatus optics, the lens support device comprising a lens wall defining a lens wall perimeter and a perimeter flange extending substantially outwardly from at least a portion of the lens wall perimeter so as to define an outwardly-facing perimeter flange surface offset from the lens wall; and
   a third lens component defining an outer third optical lens is positioned adjacent to the perimeter flange surface so as to form an air gap between the third optical lens and the lens wall of the lens support device of the second lens component.

5. The lens mount apparatus of claim 4 wherein the perimeter flange extends substantially inwardly from at least a portion of the lens wall perimeter, the perimeter flange comprising at least one mechanical attachment feature.

6. The lens mount apparatus of claim 4 wherein the first optical lens comprises two spaced-apart lens inserts formed as prescription lens blanks.

7. The apparatus of claim 4, further comprising an adhesive open-cell foam gasket positioned between the perimeter flange surface and the outer optical lens and thereby attaching the outer optical lens to the lens support device and forming a relatively larger air gap therebetween.

8. The apparatus of claim 4 wherein the second lens component is simultaneously a second optical lens, the first and second optical lenses together defining the lens mount apparatus optics.

* * * * *